(12) United States Patent
Womble et al.

(10) Patent No.: US 7,326,576 B2
(45) Date of Patent: Feb. 5, 2008

(54) RAMAN SPECTROSCOPIC MONITORING OF HEMODIALYSIS

(75) Inventors: M. Edward Womble, Watertown, MA (US); Richard H. Clarke, Boston, MA (US)

(73) Assignee: Prescient Medical, Inc., Doylestown, PA (US)

( * ) Notice: Subject to any disclaimer, the term of this patent is extended or adjusted under 35 U.S.C. 154(b) by 477 days.

(21) Appl. No.: 10/410,051

(22) Filed: Apr. 9, 2003

(65) Prior Publication Data
US 2004/0204634 A1  Oct. 14, 2004

(51) Int. Cl.
*G01N 33/62* (2006.01)
*G01N 33/50* (2006.01)
*G01N 21/65* (2006.01)
*G01J 3/44* (2006.01)
*A61B 5/20* (2006.01)

(52) U.S. Cl. ............ 436/108; 250/339.07; 250/339.12; 356/301; 436/106; 436/111; 436/164; 436/171; 600/310; 600/333; 600/366; 702/19

(58) Field of Classification Search .......... 250/339.07, 250/341.1, 339.12; 356/301, 303; 128/922, 128/925; 436/106, 108, 111, 164, 171; 600/310, 600/333, 366, 473, 475; 706/924; 702/19
See application file for complete search history.

(56) References Cited

U.S. PATENT DOCUMENTS

| | | | |
|---|---|---|---|
| 3,598,727 A | 8/1971 | Willock | |
| 3,900,396 A * | 8/1975 | Lamadrid | .................... 210/94 |
| 4,172,033 A | 10/1979 | Willock | |
| 4,267,040 A | 5/1981 | Schal | |
| 4,329,986 A * | 5/1982 | Babb | .......................... 604/5.04 |
| 4,370,983 A * | 2/1983 | Lichtenstein | ................. 600/301 |
| 4,573,761 A * | 3/1986 | McLachlan et al. | ........ 385/115 |
| 4,769,134 A | 9/1988 | Allan et al. | |
| 4,781,458 A * | 11/1988 | Angel et al. | ................. 356/301 |
| 5,011,284 A | 4/1991 | Tedesco et al. | |
| 5,139,334 A | 8/1992 | Clarke | |
| 5,372,135 A | 12/1994 | Mendelson et al. | |

(Continued)

FOREIGN PATENT DOCUMENTS

DE   4433305   * 4/1996

OTHER PUBLICATIONS

Berger, A. J. et al, Applied Optics 1996, 35, 209-212.*

(Continued)

*Primary Examiner*—Arlen Soderquist
(74) *Attorney, Agent, or Firm*—Michael V. Frank; Patton Boggs, LLP

(57) ABSTRACT

Spectroscopic systems and methods are disclosed for determining levels of at least one analyte in blood undergoing hemodialysis. In one aspect, the invention employs Raman spectroscopy to monitor and/or control hemodialysis. In one embodiment, the system uses a laser light directed to circulating blood from a patient undergoing dialysis to make Raman spectral measurements. For example, the laser light can be directed into a segment of the dialysis tubing. The system can utilize unique Raman spectroscopic signature of one or more analytes, e.g., urea, to identify and quantify such analytes against a whole blood background. Based on the spectral response, the concentration of the analytes can be monitored and/or used to control hemodialysis.

30 Claims, 6 Drawing Sheets

U.S. PATENT DOCUMENTS

| | | | |
|---|---|---|---|
| 5,534,997 A * | 7/1996 | Schrader | 356/301 |
| 5,553,616 A * | 9/1996 | Ham et al. | 600/316 |
| 5,615,673 A | 4/1997 | Berger et al. | |
| 5,621,522 A * | 4/1997 | Ewing et al. | 356/301 |
| 5,685,988 A * | 11/1997 | Malchesky | 210/646 |
| 5,697,373 A * | 12/1997 | Richards-Kortum et al. | 600/475 |
| 5,751,415 A * | 5/1998 | Smith et al. | 356/301 |
| 5,815,260 A | 9/1998 | Dou et al. | |
| 5,817,007 A * | 10/1998 | Fodgaard et al. | 600/322 |
| 5,849,179 A * | 12/1998 | Emerson et al. | 210/87 |
| 5,858,186 A * | 1/1999 | Glass | 205/777.5 |
| 5,864,397 A | 1/1999 | Vo-Dinh | |
| 5,870,188 A * | 2/1999 | Ozaki et al. | 356/301 |
| 5,982,484 A * | 11/1999 | Clarke et al. | 356/301 |
| 6,038,887 A | 3/2000 | Vild et al. | |
| 6,044,285 A | 3/2000 | Chaiken et al. | |
| 6,064,897 A | 5/2000 | Lindberg et al. | |
| 6,087,182 A | 7/2000 | Jeng et al. | |
| 6,144,444 A * | 11/2000 | Haworth et al. | 356/39 |
| 6,151,522 A * | 11/2000 | Alfano et al. | 600/473 |
| 6,154,596 A | 11/2000 | Ionov | |
| 6,156,002 A * | 12/2000 | Polaschegg et al. | 604/4.01 |
| 6,208,887 B1 | 3/2001 | Clarke | |
| 6,212,424 B1 * | 4/2001 | Robinson | 600/475 |
| 6,219,137 B1 | 4/2001 | Vo-Dinh | |
| 6,226,082 B1 | 5/2001 | Roe | |
| 6,258,027 B1 * | 7/2001 | Sternby | 600/366 |
| 6,284,131 B1 | 9/2001 | Hogard et al. | |
| 6,284,141 B1 * | 9/2001 | Shaldon et al. | 210/739 |
| H2202 H | 11/2001 | McLachlan et al. | |
| 6,313,914 B1 | 11/2001 | Roe | |
| 6,511,814 B1 | 1/2003 | Carpenter | |
| 6,560,478 B1 * | 5/2003 | Alfano et al. | 600/473 |
| 6,574,501 B2 * | 6/2003 | Lambert et al. | 600/473 |
| 6,666,840 B1 * | 12/2003 | Falkvall et al. | 604/5.04 |
| 6,721,583 B1 * | 4/2004 | Durkin et al. | 600/318 |

OTHER PUBLICATIONS

Berger, A. J. et al, Spectrochimica Acta Part A 1997, 53, 287-292.*
Berger, A. J. et al, Applied Optics 1999, 38, 2916-2926.*
Williams, K. P. J., Journal of Raman Spectroscopy 1990, 21, 147-151.*
Zimba, C. G. et al, Applied Spectroscopy 1991, 45, 162-165.*
Kneipp, K. et al, Spectrochimica Acta 1995, 51A, 481-487.*
Nava, S. E., Advances in Instrumentation and Control 1996, 51, 453-467.*
Shim, M. G. et al, SPIE 1998, 3257, 208-216.*
Walker, P. A., III et al., Journal of Chromatography A 1998, 805, 269-275.*
Qu, J. Y. et al, SPIE 2000, 3918, 174-180.*
Schultz, C. P. et al, SPIE 2000, 4129, 284-293.*
Hanlon E.B. et al. "Prospects for in vivo Raman spectroscopy," Phys. Med. Biol. 45 (2000) R1-R59.
Premasiri, W. Ranjith et al. "Urine Analysis by Laser Raman Spectroscopy," Lasers in Surgery and Medicine 28 (2001) pp. 330-334.
Clarke, R. H. et al. "Low-resolution Raman Spectroscopy as an Analytical Tool for Organic Liquids," Spectroscopy 13 (Oct. 1998) pp. 28-35 (downloaded on Jul. 31, 2003 from www.oceanoptics.com.products/ramanarticle.asp).
Clarke, R. H. et al. "Low-Resolution Raman Spectroscopy: Instrumentation and Applications in Chemical Analysis," Journal of Raman Spectroscopy 30 (1999) pp. 827-832.
Berger, Andrew J. et al. "MUlticomponent blood analysis by near-infrared Raman spectroscopy," Applied Optics 38:13 (May 1, 1999) pp. 2916-2926.
Berger, Andrew Joshua. "Measurement of analytes in human serum and whole blood samples by near-infrfed Raman spectroscopy," Ph.D. Dissertation, Massachusetts Institute of Technology, Jun. 1998.

* cited by examiner

US 7,326,576 B2

RAMAN SPECTROSCOPIC MONITORING OF HEMODIALYSIS

FIELD OF THE INVENTION

The technical field of this invention relates to methods for monitoring analyte levels in blood by Raman spectroscopy systems. More particularly, it relates to methods for monitoring urea levels in blood while a patient is undergoing hemodialysis by using Raman spectroscopy systems.

BACKGROUND OF THE INVENTION

When protein is broken down in the body, urea is produced as one of the waste products. Normally, urea is removed from the body by the kidneys and excreted as urine. However, during kidney impairment or failure, urea builds up in the body and particularly in the blood.

When kidneys fail, dialysis is necessary to remove waste products such as urea from the blood. Urea is not very toxic by itself, but its level represents the levels of many other waste products that build up in the blood when the kidneys fail. The need for a patient to undergo dialysis particularly becomes acute in end stage renal disease (ESRD). ERSD causes people to experience a total and irreversible loss of kidney function. ESRD can result from a number of conditions including nephritis, inherited diseases, hypertension and diabetes. In 1997, there were an estimated 230,000 ESRD patients in the United States. That domestic number is growing at approximately 7% annually. Worldwide data indicated that in 1997, there were approximately 157,000 patients in Western Europe, 161,000 in Japan and 230,000 throughout the rest of the world.

Unless a kidney transplant is performed on an ESRD patient, regular blood cleansing is necessary to remove harmful waste products from the blood of the patient to sustain life. Blood dialysis, in particular, hemodialysis is the most common methodology employed to accomplish the removal process. Hemodialysis artificially separates the waste products and excess water from the patient's blood by diffusion and ultra filtration. In hemodialysis, blood is circulated through a machine with a special filter that removes wastes and extra fluids. The clean blood is then returned to the body.

Most ESRD patients go to a clinic—a dialysis center—three times a week for 3 to 5 or more hours each visit. For example, a patient may be on a Monday-Wednesday-Friday schedule or a Tuesday-Thursday-Saturday schedule. The amounts of urea present in the blood, after treatment, can be measured to determine adequacy of the blood filtering procedure. Adequacy is determined by one of two parameters, denoted urea reduction ratio (URR) and dialyzer clearance (Kt/V), respectively.

Although there is no fixed number that universally represents an "adequate" hemodialysis session, it has been shown that patients live longer and have fewer hospitalizations if the URR is at least 60 percent. Considering this variation, some groups that advise on national standards have recommended a minimum URR of 65 percent. The URR is usually measured only once every 12 to 14 treatments or about once a month. The ratio may vary considerably from treatment to treatment.

In the Kt/V measurement, K represents the dialyzer clearance that is expressed in milliliters per minute (mL/min), t is for time, and V is the fluid volume. I is known that Kt/V is mathematically related to URR and is, in fact, derived from it. Kt/V also takes into account two additional factors: (1) urea generated by the body during hemodialysis and (2) the extra urea removed during hemodialysis along with excess fluid. This accounting makes Kt/V a more accurate way to measure how much urea is removed during dialysis than is URR.

However, both the URR and Kt/V techniques currently employed assessments of hemodialysis efficiency of treatment are point measurements, often not even performed at every dialysis treatment, that do not allow continuous evaluation of effectiveness. Both require blood sampling before and after treatment and require time consuming chemical analyses. As a consequence, the measurements cannot be used to determine actual urea clearance efficiency or control the extent and duration of an individual patient's dialysis session.

There is a need for reliable and precise methods for real-time, noninvasive monitoring urea in a patient.

SUMMARY OF INVENTION

The present invention provides methods for continuous monitoring the level of urea (and/or other analytes) in blood undergoing hemodialysis. Such methods can provide direct, continuous URR and/or Kt/V measurements while the patient is still attached to the hemodialysis equipment. Moreover the methods of the present invention can, in at least some instances, reduce the time a patient has to spend to undergo hemodialysis. The invention employs spectroscopic analysis, preferably low resolution Raman spectroscopy, to monitor and/or control hemodialysis.

Thus, the present invention provides spectroscopic systems and methods for monitoring levels of at least one analyte in the blood of a patient undergoing hemodialysis. In one embodiment, the system uses a laser light directed to circulating blood from a patient undergoing dialysis to make Raman spectroscopic measurements. For example, the laser light can be directed into a segment of the dialysis tubing. The system utilizes unique Raman spectroscopic signature of one or more analytes to identify and quantify such analytes against a whole blood background utilizing the spectroscopy-based systems. Based on the spectral response, the concentration of the analytes can be monitored.

BRIEF DESCRIPTION OF THE DRAWINGS

These and other objects, advantages and features of the present invention will be readily appreciated as the same becomes better understood by reference to the following detailed description when considered in connection with the accompanying drawings, in which like reference numerals designate like parts throughout the figures thereof and wherein.

DETAILED DESCRIPTION

Figure 1:
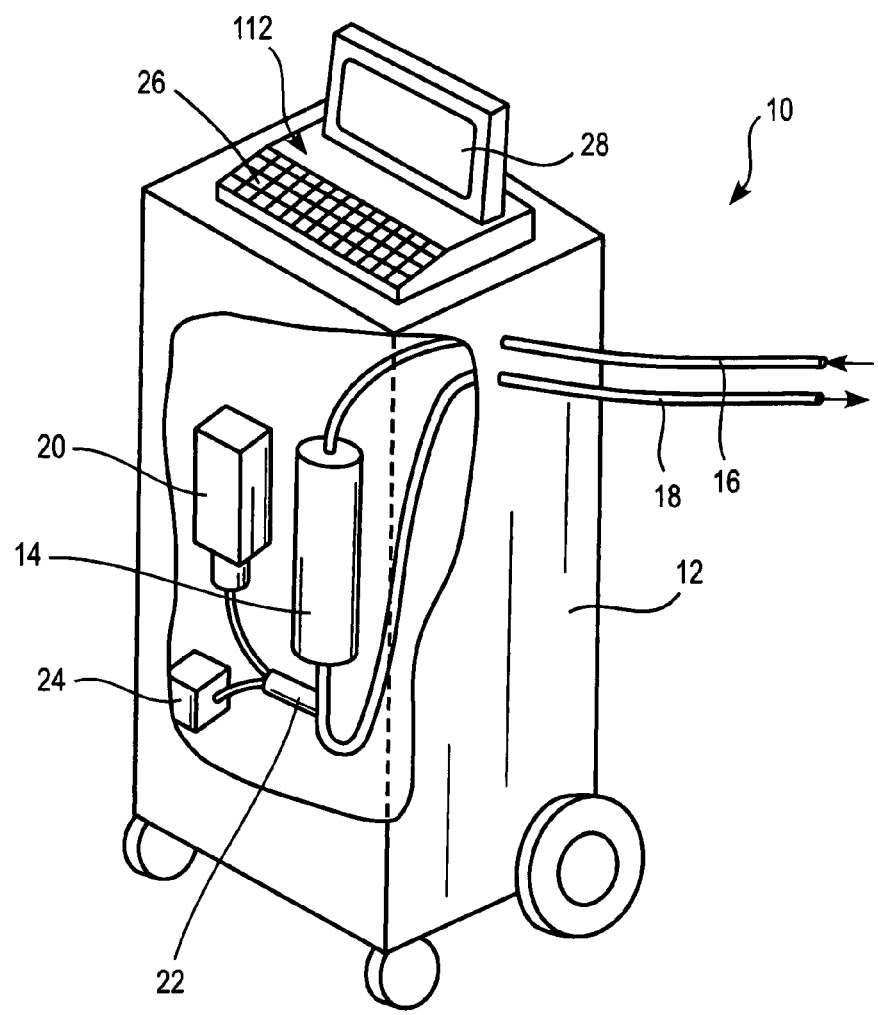
FIG. 1 is a schematic illustration of a hemodialysis system employing spectroscopic monitoring according to the invention.

Without being bound by any particular embodiment, the following discussion is offered to facilitate understanding of the invention. The present invention provides methods for monitoring levels of at least one analyte in blood of a patient undergoing hemodialysis using Raman spectroscopy, taking advantage of the optical access afforded through the clear delivery tubing connecting the patient's blood flow to the dialyzer. Unique Raman spectroscopic signature of an analyte can be identified and quantified against a whole blood background utilizing the Raman spectroscopy-based systems.

The analytes of particular interest in the present invention are the products of metabolic activity within the body of the patient. The term "analyte" as employed herein, however, can encompass any chemical composition released in the bloodstream (e.g., toxins released by microorganisms or a compound imbibed by an individual). The analyte contained in the blood may be a specific analyte or a combination of a species of analyte or a specific analyte with other components which are metabolized. The concentration of analyte within the body can increase or decrease, as a result of an impaired organ function. Any change in threshold value of the analyte concentration is indicative of a patient being at risk of an impaired organ function and would adversely affect the patient (e.g., analytes could act as toxins). In general, the analytes which are utilized under the precepts of the invention may be anabolites or products of a constructive metabolic process, or catabolites, or products which, by a destructive metabolic process, are converted into excreted compounds. In one embodiment, the analytes are selected to provide a measurement of blood urea nitrogen in the bloodstream. In this regard, the analyte can be selected from the group consisting of urea-based compounds, urea nitrogen-based compounds, ammonium-based compounds, uric acid-based compounds, and nitrogen-based compounds. Of that group, the preferred analyte contained in the blood is urea. Hence, in one embodiment, the methods of present invention are directed to monitoring the levels of urea or blood urea nitrogen in patients undergoing dialysis. The term "level" or "levels" of an analyte, as used herein, refers to concentration of a constituent, especially as a constituent of a body fluid (e.g., blood analyte). The concentration levels are readily derivable from spectral measurements. Thus, the "level" can also be measured based on the spectral data without the need, in all instances, to convert such data into concentration values. The term "level" is also meant to include the magnitude of a quantity considered in relation to an arbitrary reference value. For example, a look-up table can be used for plotting urea predictions versus a reference comprising of healthy individuals or threshold concentrations in healthy individuals.

Thus, in one embodiment, the present invention provides methods for monitoring levels of at least one anabolic or a catabolic analyte in a blood sample of an individual. The methods of the present invention include irradiation of the blood sample with light to produce spectrum and use a monitoring system to analyze the spectrum. In a preferred embodiment, the systems are configured to monitor the blood for the presence of an analyte by changes in intensity of reflected or scattered light at particular wavelengths. The intensity changes induced by an analyte may be identified by probes.

The spectroscopy system is preferably a Raman spectroscopy system, which can have inherent advantages over infrared and visible spectrum spectroscopy insofar as aqueous solutions are difficult to resolve using conventional spectroscopy and even near-infrared typically provides less reliable data than Raman measurements. More preferably, in some applications, the Raman spectroscopy system is a low resolution systems that measures Raman scattered light in the near infrared region of the spectrum.

Probes for analyzing analytes in Raman spectroscopy systems are well known in the art. An example of such a probe can be found in a commonly owned, co-pending, U.S. patent application Ser. No. 10/367,238 entitled "Probe Assemblies for Raman Spectroscopy" filed Feb. 14, 2003, which is incorporated herein in its entirety by reference. In a preferred embodiment, the system is a low resolution Raman spectroscopy system (LRRS), which utilizes low-resolution Raman scattering for the direct measurement of urea level in the blood using optical access provided by the dialysis tubing (e.g., a transparent dialysis tubing) delivering the patients blood to the dialyzer or from the dilayzer back to the patient.

The source of light will depend upon the spectroscopy system chosen. Lasers are particularly useful light sources because they are capable of producing tightly-focused light in a specific region of the electromagnetic spectrum. These include a far infrared, mid infrared, infrared, near infrared, visible light, ultra-violet, and extreme-ultraviolet. In one preferred embodiment, a near infrared laser is used in a low resolution Raman spectroscopy system (LRRS), resolution details are relinquished in favor of emphasizing essential identifying basic spectral features, which simultaneously lessens the demands on the excitation source. Although Raman spectroscopy is preferred, it should be clear that other spectral measurements, including conventional, infrared or visible light, absorption, reflection or transmission spectroscopy, can also be used in accordance with the present invention.

In a typical LRRS application the use of multi-mode lasers causes a degradation in the resolution of the spectrometer. The resolution of the LRRS system decreases primarily because the width of the laser line used to excite the analyte is much larger with multi-mode lasers than it is with a single mode laser. A multi-mode laser has a linewidth on the order of about 1 nanometer. In comparison, a single mode laser has a linewidth of a fraction of a nanometer. However, one rarely requires single wavenumber resolution to find a spectral fingerprint feature that allows identification and quantification of an analyte under analysis. Similarly, in LRRS, since the approach uses fundamental frequencies, even if not fully resolved, in the spectral analysis, a broader band laser source may suffice for the Raman analysis. In this case inexpensive, multi-mode solid state laser sources are both sufficient for the task and cost effective, and high power is the preferred source of laser light in the present invention.

A complete LRRS spectroscopic system can consist of an inexpensive multi-mode laser diode operating at a higher power (e.g., between 50 mw and 1000 mw output) than traditional single-mode Raman sources and a low resolution monochromator matched to a simple CCD detector, with Rayleigh filtering provided by notch filters capable of removing the excitation source background. U.S. Pat. No. 5,139,334 issued to Clarke, and incorporated herein by reference, teaches a low resolution Raman spectral analysis system for determining properties related to hydrocarbon content of fluids. The system utilizes a Raman spectroscopic measurement of the hydrocarbon bands and relates specific band patterns to the property of interest. U.S. Pat. No. 6,038,887, also issued to Clarke, and incorporated herein by reference, provides low resolution Raman spectroscopic systems and methods for in-vivo detection and analysis of a lesion in a lumen of a subject. The present invention utilizes similar systems for detecting levels of analytes in blood samples based on a change in the Raman scattered radiation produced in the presence of at least one analyte (e.g., urea) in the blood of a patient.

In a preferred embodiment, present invention provides a method for continuous monitoring of urea levels using a continuous, noninvasive optical technique, taking advantage of the optical access afforded through the clear delivery tubing connecting the patient's blood flow to the dialyzer. A preferred optical method to successfully accomplish this analysis is low resolution laser Raman scattering. Urea has a unique Raman spectroscopic signature and can be identified and quantified against a whole blood background.

Because of the analyte concentration monitoring approach of the present invention is utilized in conjunction with blood flowing through a dialysis tubing, the system may be automated to perform under controller-based technology. Such technology permits, in turn, the generation of substantial additional data, for example, involving operator inserted threshold values, threshold rates of change of measured values and associated warnings and alarms and, additionally the outputting of trending data providing the practitioner with a graphical or least numerical view of patient progress or lack thereof.

The Raman spectroscopic measurement approach allows real-time, continuous monitoring of the progress of urea removal during the course of hemodialysis. Thus permit more efficient timing of the dialysis procedure for the patient, as well as providing an ongoing readout of the effectiveness of the dialysis system during patient treatment. The blood from a patient undergoing dialysis can be monitored at any point during dialysis. It may be monitored continuously or at different time intervals. For example, it may be monitored at intervals between 1 and 5 minutes (min), 5 and 15 min, 15 and 30 min, 30 and 60 min or it may be monitored between 1 and 2 hours, after dialysis has begun. It can be monitored once the blood has been removed from the body for cleansing and after it has been cleansed by the dialyzer. For example, it may be monitored before the blood enters a dialyzer or after it has passed through it. It can also be monitored both before and after the blood has been cleansed by the dialyzer. Preferably, blood may be monitored as it is allowed to flow, a few ounces at a time, through the dialyzer, with every ounce of blood that flows out being monitored for the levels of an analyte. If necessary, monitoring of blood may continue until adequacy of the blood filtering process is determined by spectroscopy. This may include re-administering of dialysis treatment. Kidney dialysis machines are well known in the art and are illustrated, for example, in U.S. Pat. Nos. 3,598,727, 4,172,033, 4,267,040, and 4,769,134 and 6,284,131, and are incorporated herein by reference.

Figure 3:
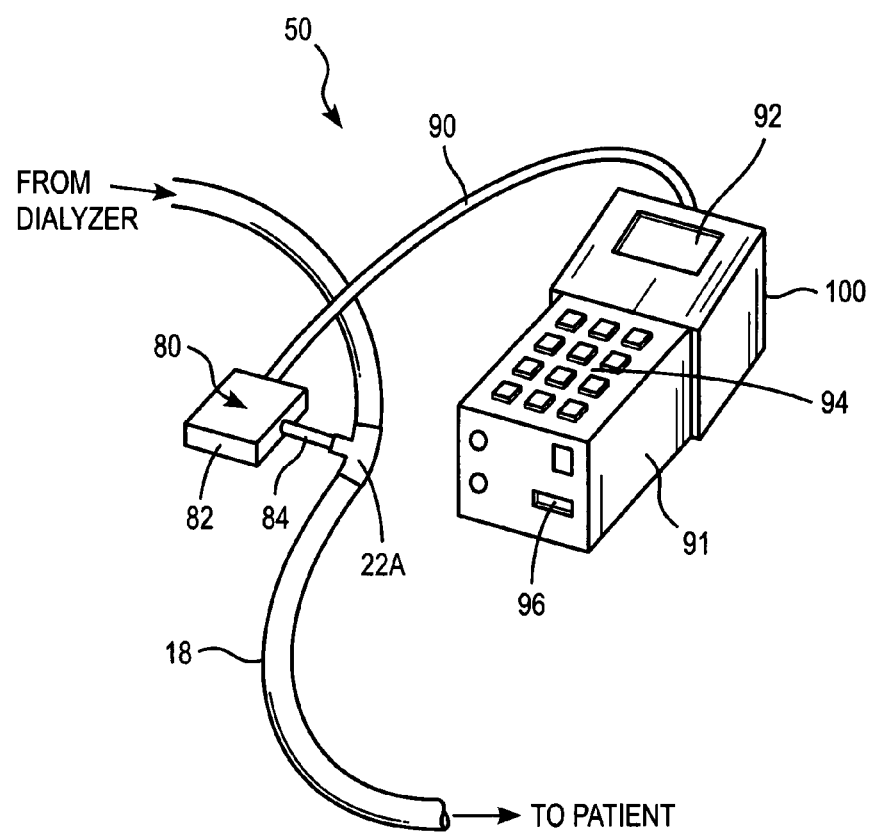
FIG. 3 is a schematic diagram of an alternative spectroscopic hemodialysis monitoring system according to the invention.

FIG. 1 is a schematic illustration of a hemodialysis system 10 having a dialyzer filter 14 within a housing 12. The system 10 further includes inflow tube 16 and outflow tube 18 which deliver blood from a patient undergoing dialysis to the filter 14, and return filtered blood back to the patient, respectively. FIG. 3 shows an example of an overall Raman spectroscopy system 50 which can be used in the present invention. The system further includes a probe 22, preferably coupled to the outflow tube exiting filter 14 and in optical communication with the blood flowing in tube 18. The optical monitoring apparatus of the invention can further include a light source 20 and a spectrometer or similar analyzing instrument 24. This system 10 can include a microprocessor 112 for controlling various filtration functions in response to signals from the spectrometer 24 and various other sensors. The system can further include a display 28, and a keyboard or other user interface 26, as well as one or more communication ports for receiving or downloading data from other sources.

Figure 2:
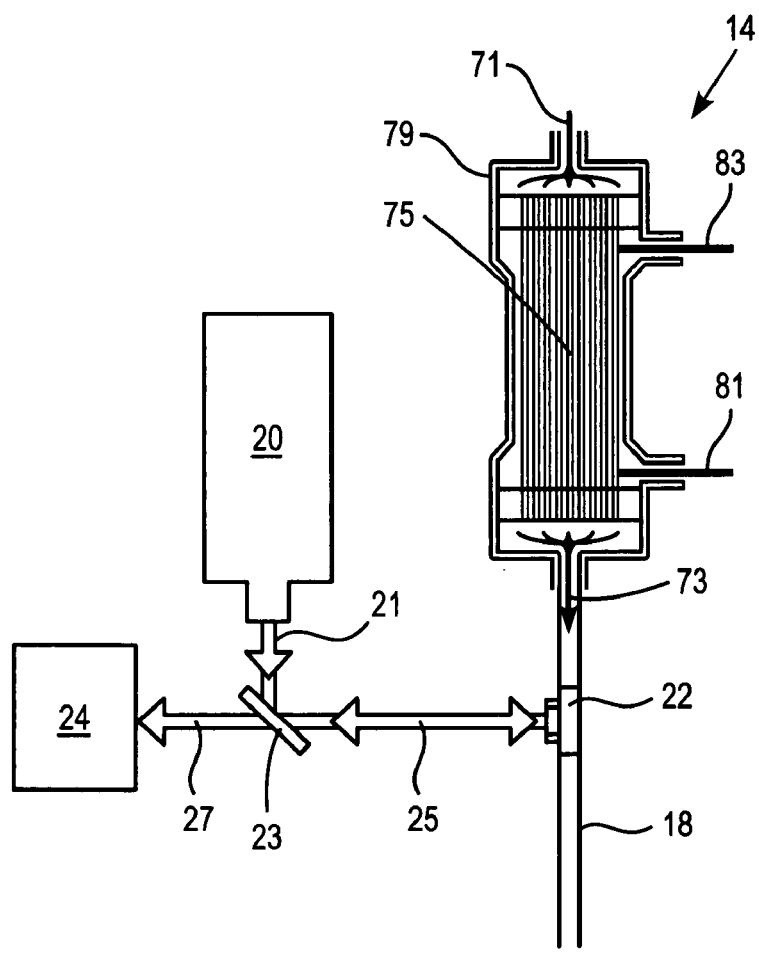
FIG. 2 is a more detailed schematic diagram of a spectroscopic hemodialysis monitoring system according to the invention.

In FIG. 2, a more detailed schematic diagram of the dialyzer filter and optical components is presented, showing filter 14 having a housing 79, a blood inlet 71, and a blood exit port 73. Within the housing 79 the blood flows inside hollow, semi-permeable fibers 75. The fibers are bathed in a circulating dialyzer solution, e.g., introduced via entry port 81 and withdrawn via exit port 83. The walls of the fibers permit the selective passage of urea and other metabolic waste products from the blood into the dialyzer solution. (It should be clear that the illustrated dialysis system is schematic and that various alternative systems can be employed to achieve the same result—fluid purification.)

Again, with reference to FIG. 2, an optical probe 22 is coupled to the exit tube 18. In the monitoring assembly, light from light source 20 (e.g., a low power laser) is directed along beam path 21 to dichroic mirror 23, where it is turned by reflection and directed to the probe 22 along beam path 25. When the excitation radiation impinges on the blood, a portion of the radiation is scattered at various Raman wavelengths. A portion of this radiation is collected (e.g., via optical elements, not shown) and retransmitted back along path 25. At the dichroic mirror 23, the wavelengths of radiation that are of interest pass through the mirror and continue along beam path 27 to the detector module 24.

In FIG. 3, an alternative analyzer system 50, especially useful for portable applications, is shown. The system 50 includes a probe 80 with its optical head assembly 82 and sampling tube 84 as well as a handheld analyzer/laser assembly 100. The probe 80 and the sampling tube 84 can be placed in cross proximity to a transparent dialysis tube 18 through which blood containing an analyte is flowing, and coupled to the tube 18 via probe coupler 22A, to deliver excitation light. The sampling tube 84 serves to collect radiation scattered by the blood and more specifically by the analytes, such as urea, in response to a excitation beam from a laser housed within the handheld analyzer/laser assembly 100. The collected radiation is delivered via optical fiber bundle 90 to assembly 100 and the concentration of an analyte in blood of a patient undergoing hemodialysis is analyzed by the Raman spectroscopy system 50. This system can include a handheld instrument 91 having a display 92, a keyboard or other user interface 94, and one or more communication ports 96 for receiving or downloading data from other sources.

Figure 4:
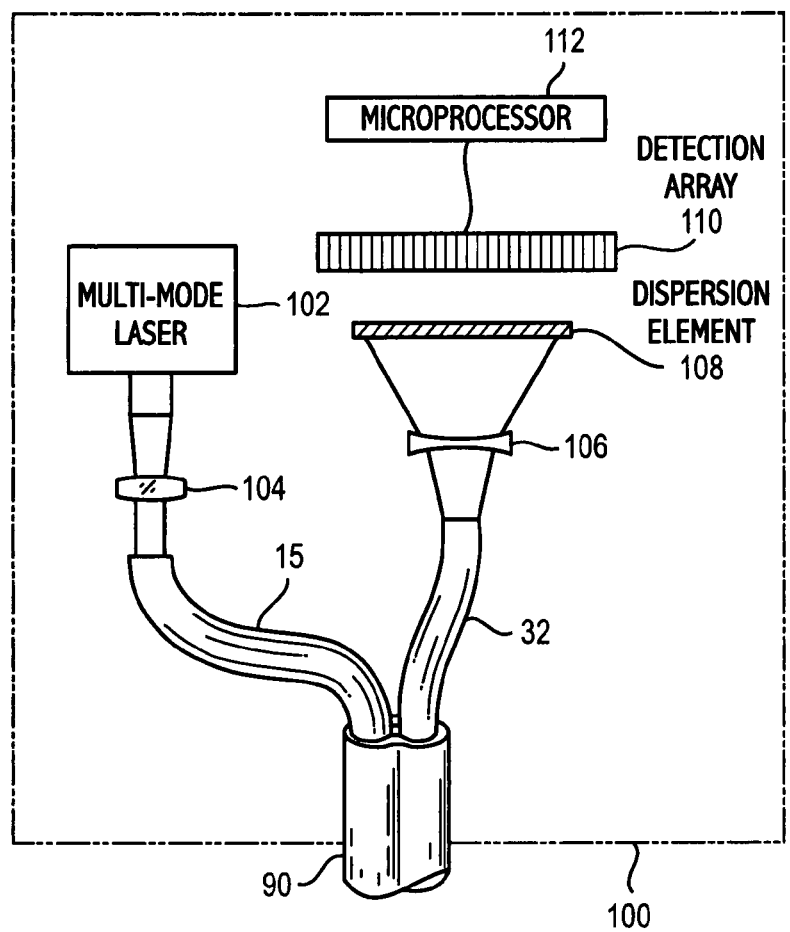
FIG. 4 is a schematic block diagram of a system according to the invention employing Raman scatter spectroscopy.

FIG. 4 is a schematic diagram of a laser/analyzer system 100 that is particularly well-suited for use with the probes of the present invention to perform sampling operations. System 100 includes a multi-mode laser source 102 and optional relay optics 104 connected to an excitation optical fiber 15 that carries the laser light to the probe. The laser source 102 can be one of many multi-mode laser sources. For example, the B&W Tek multi-mode laser BWF-OEM-785-0.5, available from B&W Tek, Inc., of Newark, Del., can be used as the multi-mode laser. The Raman scattered light is collected by the probe and delivered via flexible optical fiber 32 to the analyzer assembly of system 100. The Raman scattered light travels through the fiber 32 (and optically via relay optics 106) into a low-resolution dispersion device 108 that serves to disperse the scattered light into its different wavelength components. The dispersed scattered light is detected by photodetector array 110 that, in this case, consists of a photodiode array or a charged-coupled device (CCD) array. The signals generated by the detector array 110 in response to the scattered light captured by the probe are then sent to a microprocessor 112 for analysis.

In the system 100, specific spectral bands of interest can be measured at low resolution to obtain the integrated band intensities. These bands can be narrow ones. The resolving power of the dispersion device 108 determines the position of specific wavelengths in the diode array in such a way that the signal from a particular diode in the array will typically correspond to the same (or a similar) narrow range of wavelengths. This combination of the low-resolution dispersion device 108 and the diode array photodetector 110 thus form a spectrometer. The microprocessor 112 selects a particular diode (or diodes) of the array 110 according to the property to be measured. The integrated signals lying in the two ranges can be arithmetically divided to form intensity ratios. The microprocessor 112 compares these ratios with known values or a correlating function to obtain an estimate of the chemical constituent or property of interest.

The terms "radiation" and "light" are herein utilized interchangeably. In particular, the term "light" can refer to radiation having wavelength components that lie in the visible range of the electromagnetic spectrum, or outside the visible range, e.g., the infrared or ultraviolet range of the electromagnetic spectrum. In certain embodiments of Raman spectroscopy, the preferred excitation wavelengths will range from about 700 nanometers to 2.5 micrometers. Although this portion of the electromagnetic spectrum is commonly known as infrared (IR) radiation, the term "light" will be used as shorthand expression in describing the path of this radiation as well as the various wavelengths of radiation induced by Raman scattering and collected for analysis.

Advances in the field of solid state lasers have introduced several important laser sources into Raman analysis. For high-resolution Raman systems the laser linewidth must be severely controlled, often adding to the cost of the excitation source and the system as a whole. For low resolution Raman spectroscopy (LRRS), however, the strategy of relinquishing resolution details in favor of emphasizing essential identifying spectral features, allows the use of a low cost, high energy multi-mode laser and a low resolution dispersion element. A multi-mode laser which can be used with a LRRS system, according to one embodiment of the present invention, is available in higher power ranges (between 50 mw and 1000 mw) than is available with a traditional single mode laser (<150 milliwatts). The higher power of a multi-mode laser increases the amount of scattered radiation available to the spectrometer system. The sensitivity of the LRRS system increases at least linearly with laser power.

A low resolution dispersion element can provide greater transmission of scattered radiation to the detector array. For example, a low resolution diffraction grating with wider slits than a typical diffraction grating can be used, providing greater transmission of incident scattered radiation to a detector array. The combination of a high energy multi-mode laser and a low loss dispersion element can provide an inexpensive LRRS system with a high intensity signal.

In a typical LRRS application the need for feature separation is much like that encountered in mid-IR spectroscopy. The use of multi-mode lasers causes a degradation in the resolution of the spectrometer. The resolution of the LRRS system decreases primarily because the width of the laser line used to excite the sample is much larger with multi-mode lasers than it is with a single mode laser. A multi-mode laser has a linewidth of 2-3 nanometer. In comparison, a single mode laser has a linewidth of a fraction of a nanometer. However, one rarely requires single wavenumber resolution to find a spectral fingerprint feature that allows identification and quantification of a sample under analysis. Similarly, in LRRS, since the approach uses fundamental frequencies, even if not fully resolved, in the spectral analysis, a broader band laser source may suffice for the Raman analysis. In this case inexpensive, multi-mode solid state laser sources are both sufficient for the task and cost effective, and high power.

Since a Raman measurement is the difference in wavelength between the scattered light and the excitation line, an excitation line that has a larger spectral FWHM causes a proportional loss of resolution in the resulting Raman measurement. However, this reduction of resolution is offset by the advantages of lower cost and increased signal intensity. The increased signal intensity is a result of a higher energy laser source and wider slits in the diffraction grating allowing more light into the detector array. Since the spectrometer system resolution has been substantially reduced by the use of a multi-mode laser, the width of the slits can be increased with negligible effect on resolution. In addition, a CCD detector array can be matched to the lower resolution laser source and the dispersion element by reducing the number of elements in the array. For example, instead of 4096 array elements, one can use 2048 larger elements.

Thus, a complete LRRS spectroscopic system can consist of an inexpensive multi-mode laser diode operating at a higher power (between 50 mw and 1000 mw output) than traditional single-mode Raman sources and a low resolution monochromator matched to a simple CCD detector, with Rayleigh filtering provided by edge or notch filters capable of removing the excitation source background.

Various low resolution monochromators can be used as detector arrays. For example, Ocean Optics S-1000 and S-2000 monochromators are commercially available from Ocean Optics of Dunedin, Fla. Optical filters can be used to eliminate the Rayleigh line.

The optical fibers utilized in the probe apparatus of the invention can be multimode fibers, which are available from several commercial sources including, for example, Fiberguide, Inc. of Sterling, N.J. Their diameters may range from 1 μm to 1000 μm, preferably from about 100 μm to about 400 μm, and more preferably from about 100 μm to about 200 μm. Single fibers and fiber bundles can be utilized in the present invention.

Figure 5:
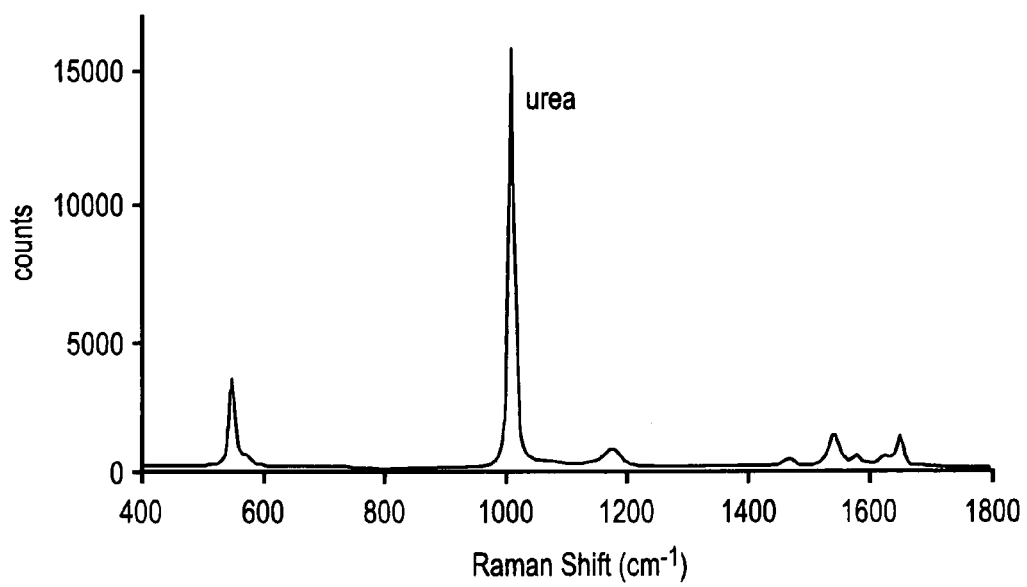
FIG. 5 is a graph of the Raman spectrum of urea.

FIG. 5 is a graph showing the spectrum of pure urea obtained from low resolution Raman spectroscopy. The peak near 1000 $cm^{-1}$ is clearly a pronounced spectral feature and, in accordance with the present invention, can be used for urea identification and analysis. This band corresponds to the symmetrical CN stretch and is the main observable peak at clinical concentration levels.

To investigate the ability to detect urea levels against a more chemically challenging background of blood, Raman spectra of urea in blood plasma were obtained. A series of Raman spectra were run on a commercially obtained (Sigma Chemical) human blood plasma sample to which increasing amounts of urea were added. Resulting spectra show that despite the presence of a nearby interfering peak (at 1000 cm−1, due to the aromatic-containing protein phenylalanine), the urea spectrum was evident in the blood plasma sample and fully identifiable in the low resolution regime. These results are graphically illustrated in FIG. 6, which shows how a linear correlation between the peak height at 1001 cm$^{-1}$ and urea concentration.

Figure 6:
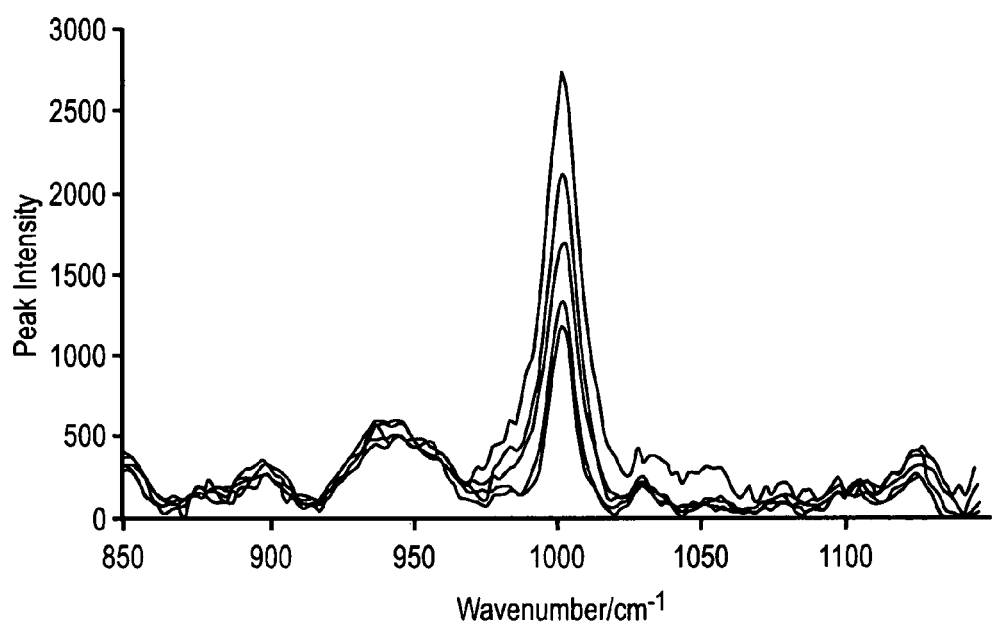
FIG. 6 is a graph showing Raman spectra for blood samples having varying concentrations of urea.
Figure 7:
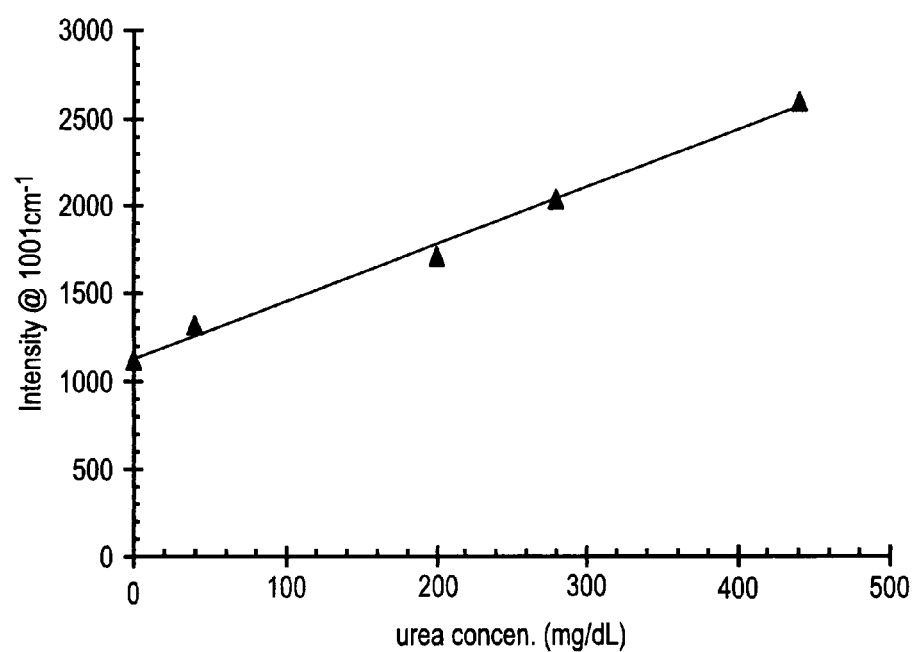
FIG. 7 is graph of the measured intensity of scattered radiation (at 1001 cm$^{-1}$) versus urea concentration for the spectra shown in FIG. 6.

FIG. 7 is graph of the measured intensity of scattered radiation (at 1001 cm$^{-1}$) versus urea concentration for the spectra shown in FIG. 6. The latter result demonstrates the ability of Raman to produce a concentration correlation, since a linear response is the most basic of analytical statistical tools available for extracting urea concentration from the Raman spectral features.

We claim:

1. A method for monitoring hemodialysis, the method comprising the steps of:
    adapting a Raman spectroscopy probe to a hemodialysis tube of a hemodialysis system;
    irradiating a sample of blood in the tube that is undergoing hemodialysis by the system with light via the probe;
    obtaining a Raman spectrum of chemical constituents from the sample via the probe; and
    determining the concentration of urea in the sample based on a linear correlation between urea concentration and intensity of Raman scattered light at 1001 cm$^{-1}$.

2. The method of claim 1, further comprising: repeating the steps of irradiating and analyzing to detect changes in level of the analyte over time.

3. The method of claim 1, wherein the step of irradiating the sample further comprises irradiating the sample with light of at least one wavelength in the range from about 700 nanometers to about 2.5 micrometers.

4. The method of claim 1, wherein the step of irradiating the sample further comprises irradiating the sample with light from a multi-mode laser.

5. The method of claim 1, wherein the step of irradiating the sample further comprises irradiating the sample with a broad band light source.

6. The method of claim 1, wherein the step of irradiating the sample further comprises irradiating the sample with infrared light.

7. The method of claim 1, wherein the step of obtaining a Raman spectrum of light scattered by the sample comprises detecting Raman scattered light using low resolution detector.

8. The method of claim 1, wherein the step of analyzing the spectrum further comprises determining the concentration of at least one analyte other than urea in the sample.

9. The method of claim 8, wherein the analyte other than urea comprises an analyte selected from a group consisting of: a urea-based compound, an ammonium-based compound, a uric acid-based compound, and a nitrogen-based compound.

10. The method of claim 1, wherein the Raman spectroscopy probe comprises an optical head assembly that is operably connected by an optical fiber bundle to a light source and a light analyzer.

11. The method of claim 10, wherein the Raman spectroscopy probe further comprises a sampling tube connected to the optical head assembly and the step of adapting the Raman spectroscopy probe to the hemodialysis tube further comprises coupling the sampling tube to the hemodialysis tube using a coupler.

12. The method of claim 1, wherein the step of adapting the Raman spectroscopy probe to the hemodialysis tube comprises coupling the probe to the tube using a coupler.

13. The method of claim 12, wherein the Raman spectroscopy probe comprises an optical head assembly that is operably connected by an optical fiber bundle to a unit comprising a laser source and a light analyzer.

14. The method of claim 1, wherein the Raman spectroscopy probe comprises:
    an optical head assembly that defines a light input pat and a light output path that are at least substantially orthogonal; and
    a light redirecting element that redirects light from the input path toward the sample and transmits light from the sample to the output path.

15. The method of claim 14, wherein the light directing element comprises a dichroic mirror.

16. A method for monitoring a subject's urea concenintion, the method comprising the steps of:
    irradiating a blood sample from a subject using a Raman spectroscopic probe comprising:
        an optical head assembly that defines a light input path and a light output path that are at least substantially orthogonal, and
        a light redirecting element that redirects light from the input path toward the sample and transmits light from the sample to the output path;
    collecting a Raman spectrum of light scattered by the sample; and
    analyzing the intensity of the Raman spectrum at 1001 cm$^{-1}$ to detect the concentration of urea in the sample using a linear correlation between intensity of the Raman spectrum at 1001 cm$^{-1}$ and the concentration of urea, the concentration of urea being indicative of the progress of dialysis or kidney function.

17. The method of claim 16, further comprising: repeating the steps of irradiating and analyzing to detect changes in urea concentration over time.

18. The method of claim 16, wherein the decrease in concentration of urea is indicative of elimination of toxins from the blood sample during dialysis.

19. The method of claim 16, wherein the Raman spectrum is analyzed by a low resolution Raman spectroscopy system.

20. The method of claim 16, wherein the sample is present within an at least substantially transparent tube.

21. The method of claim 20, further comprising the step of coupling the probe to the tube using a coupler.

22. The method of claim 16, wherein the light directing element comprises a dichroic mirror.

23. A hemodialysis system comprising:
    at least one blood cleaning element for removing toxins from blood;
    hemodialysis tubing;
    a light source to irradiate a sample of blood in the hemodialysis tubing that is undergoing hemodialysis;
    a Raman spectrometer to detect Raman scattered light of at least one analyte in the sample including urea, the concentration of the analyte being indicative of the progress of hemodialysis; and
    a Raman spectroscopy probe mediating optical communication between the light source and the sample of blood in the hemodialysis tubing and between the Raman spectrometer and the sample of blood in the hemodialysis tubing,
    wherein the system is configured to determine urea concentration in the sample based on a linear correlation between urea concentration and intensity of Raman scattered light at 1001 cm$^{-1}$.

24. The system of claim 23, wherein the system further comprises a processor that controls hemodialysis based, at least in part, on data from the Raman spectrometer.

25. The system of claim 23, further comprising a probe coupler that couples the probe to the tubing.

26. The method of claim 25, wherein the Raman spectroscopy probe comprises an optical head assembly that is operably connected by an optical fiber bundle to a light source and a light analyzer.

27. The method of claim 23, wherein the Raman spectroscopy probe comprises an optical head assembly that is operably connected by an optical fiber bundle to a light source and a light analyzer.

28. The method of claim 27, wherein the Raman spectroscopy probe further comprises a sampling tube connected to the optical head assembly and the probe is coupled to the hemodialysis tubing via the sampling tube.

29. The method of claim 23, wherein the Raman spectroscopy probe comprises:
   an optical head assembly that defines a light input path and a light output path that are at least substantially orthogonal; and
   a light redirecting element that redirects light from the input path toward the sample and transmits light from the sample to the output path.

30. The method of claim 29, wherein the light directing element comprises a dichroic mirror.

* * * * *